United States Patent
Spangler et al.

(10) Patent No.: US 11,269,929 B2
(45) Date of Patent: Mar. 8, 2022

(54) COMBINING SEMANTIC RELATIONSHIP INFORMATION WITH ENTITIES AND NON-ENTITIES FOR PREDICTIVE ANALYTICS IN A COGNITIVE SYSTEM

(71) Applicant: International Business Machines Corporation, Armonk, NY (US)

(72) Inventors: William S. Spangler, San Martin, CA (US); Richard L. Martin, Jamaica Plain, MA (US); David Martinez Iraola, Sunnyvale, CA (US); Daniel Pierce, Rochester, MN (US); Sheng Hua Bao, San Jose, CA (US); Meenakshi Nagarajan, San Jose, CA (US); Michael D. Pfeifer, Olmsted, MN (US)

(73) Assignee: International Business Machines Corporation, Armonk, NY (US)

( * ) Notice: Subject to any disclaimer, the term of this patent is extended or adjusted under 35 U.S.C. 154(b) by 188 days.

(21) Appl. No.: 15/971,207

(22) Filed: May 4, 2018

(65) Prior Publication Data

US 2019/0340294 A1 Nov. 7, 2019

(51) Int. Cl.
*G06F 17/30* (2006.01)
*G06F 16/28* (2019.01)
(Continued)

(52) U.S. Cl.
CPC ........ *G06F 16/288* (2019.01); *G06F 16/9024* (2019.01); *G06F 40/30* (2020.01); *G06N 5/022* (2013.01); *G16B 50/00* (2019.02)

(58) Field of Classification Search
CPC .. G06F 16/24575; G06F 16/55; G06F 16/783; G06F 16/288; G06F 40/30;
(Continued)

(56) References Cited

U.S. PATENT DOCUMENTS 8,818,929 B2 8/2014 Fraboulet-Laudy et al.
9,436,760 B1 * 9/2016 Tacchi ................... G06N 5/022
(Continued)

OTHER PUBLICATIONS

Neville et al., "Iterative Classification in Relational Data", 2000, University of Massachusetts. (Year: 2000).*

(Continued)

*Primary Examiner* — Hung D Le
(74) *Attorney, Agent, or Firm* — Edell, Shapiro & Finnan, LLC (57) ABSTRACT

According to embodiments of the present invention, methods, systems and computer readable media are provided, in a cognitive data processing system, for implementing a predictive analytics system that utilizes entity and non-entity information. A collection of content is processed to extract defined entities pertaining to one or more domains. Semantic relationships are determined between objects within the collection of content, wherein the objects include undefined entities. The defined entities and objects are resolved based on entity definitions and the semantic relationships to determine defined entities and undefined entities for a resulting data set. The resulting data set is processed to identify one or more relationships between a defined entity and an undefined entity.

20 Claims, 6 Drawing Sheets

| | | OBJECT | |
|---|---|---|---|
| | | ENTITY | NON-ENTITY |
| SUBJECT | ENTITY | ENTITY TO ENTITY (TRADITIONAL RELATIONSHIP NETWORK) | ENTITY TO NON-ENTITY |
| | NON-ENTITY | NON-ENTITY TO ENTITY | NON-ENTITY TO NON-ENTITY |

(51) Int. Cl.
*G06N 5/02* (2006.01)
*G06F 16/901* (2019.01)
*G16B 50/00* (2019.01)
*G06F 40/30* (2020.01)

(58) Field of Classification Search
CPC .. G06F 16/9024; G06F 16/3344; G06F 16/36; G06F 40/216; G06F 40/295; G06F 16/13; G06F 16/24; G06F 16/156; G16B 50/00; G16B 50/10; G06N 5/022; G06N 20/00; G06N 3/00; G06N 5/00; G05B 13/00
See application file for complete search history.

(56) References Cited

U.S. PATENT DOCUMENTS

| | | | |
|---|---|---|---|
| 9,594,825 B2 | 3/2017 | Skarin et al. | |
| 9,710,544 B1* | 7/2017 | Smith | G06F 40/30 |
| 2003/0105638 A1* | 6/2003 | Taira | G10L 15/005 |
| | | | 704/275 |
| 2008/0275833 A1* | 11/2008 | Zhou | G06N 7/005 |
| | | | 706/45 |

OTHER PUBLICATIONS

Altinel et al., "A Semantic Kernel for Text Classification Based on Iterative Higher-Order Relations between Words and Documents", 2014, Springer. (Year: 2014).*

Song et al., "Unsupervised Sparse Vector Densification for Short Text Similarity", 2015, Association for Computational Linguistics. (Year: 2015).*

Nickel, M. et al.; "A Review of Relational Machine Learning for Knowledge Graphs"; arXiv: 1503.00759v3; Maximilian University Munich; Sep. 28, 2015.

Gomez-Perez, JM. et al.; "Enterprise Knowledge Graph: An Introduction" in Exploiting Linked Data and Knowledge Graphs in Large Organizations, Eds. Pan, J.Z. et al., Switzerland, Springer International Publishing (2017) p. 1-14.

Anonymously; "A System and Method for Annotation of Semantic Relations that Span Multiple Documents"; http://ip.com/IPCOM/000231089D; Sep. 25, 2013.

Anonymously; "Method and System for Representation of Industry Standard Concepts for Semantic Modeling" http://ip.com/IPCOM/000197637D; Jul. 19, 2010.

Anonymously; "Natural Language Semantics in Support of Knowledge Base Searching and Computer Aided Troubleshooting"; http://ip.com/IPCOM/000246121D; May 10, 2016.

https://developers.google.com/knowledge-graph/ (retrieved from the web May 4, 2018).

Velardi, et al., "Ontolearn reloaded: A graph-based algorithm for taxonomy induction." Computational Linguistics, vol. 39, No. 3 (2013): 665-707.

Ramakrishnan, et al., "A framework for schema-driven relationship discovery from unstructured text." The Semantic Web ISWC (2006): 583-596.

"Release information", IBM Watson for Drug Discovery, version 2.86, released Jun. 2017 (accessed May 3, 2018), 2 pages.

"Getting Started", IBM Watson for Drug Discovery, version 2.86, released Jun. 2017 (accessed May 3, 2018), 1 page.

* cited by examiner

|  | OBJECT | |
|---|---|---|
|  | ENTITY | NON-ENTITY |
| SUBJECT ENTITY | ENTITY TO ENTITY (TRADITIONAL RELATIONSHIP NETWORK) | ENTITY TO NON-ENTITY |
| NON-ENTITY | NON-ENTITY TO ENTITY | NON-ENTITY TO NON-ENTITY |

COMBINING SEMANTIC RELATIONSHIP INFORMATION WITH ENTITIES AND NON-ENTITIES FOR PREDICTIVE ANALYTICS IN A COGNITIVE SYSTEM

BACKGROUND

1. Technical Field

Present invention embodiments relate to predictive analytics, and more specifically, to generating semantic relationships between entities and non-entities for complex predictions using a cognitive system.

2. Discussion of the Related Art

In the modern computing era, computational techniques and systems allow for complex analysis on large volumes or corpuses of data. Natural language processing and machine learning systems may be used to extract, analyze, and make inferences or predictions on such data.

Natural language processing techniques may utilize semantic analysis to understand semantic relationships. Often, semantic relationship analysis is limited to analyzing relationships between entities. Current solutions for semantic relationship extraction from text rely on grounding extracted information into concepts (entities). Entity-based semantic relationship extraction from text is a well-known technology that has been used for building knowledge graphs, ontologies, as well as the discovery of new relationships.

For example, a typical semantic relationship network in a biological domain may connect genes to other genes, genes to proteins, and so on. However, this traditional entity network is limited by its reliance on pre-defined entities and entity types. For example, a gene and protein entity network will not comprise any connections involving concepts that are not genes and proteins. Although new entity types can be added to a network, this process is time consuming and does not address the fundamental limitation of information loss in entity-based networks, as entities comprise only a small fraction of the information that is present in a data source. In a natural language corpus of information, there are many non-entity phrases that are used in the discussion of an entity or in other contexts that can provide valuable information in regards to a search or query regarding the entity.

Thus, existing methods for semantic analytics typically utilize only entity-to-entity relationship data, and are limited in their ability to make complex predictions due to information loss.

SUMMARY

According to embodiments of the present invention, which include methods, systems and computer readable media, a cognitive data processing system is provided which utilizes relationships between entities and non-entities to generate predictions. A collection of content is processed to extract defined entities pertaining to one or more domains. Semantic relationships are determined between semantic objects within the collection of content, wherein the semantic objects may include undefined entities. The defined entities are resolved with semantic objects based on entity definitions and the semantic relationships to determine defined entities and undefined entities for a resulting data set. The resulting data set is processed to identify one or more relationships between a defined entity and an undefined entity.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components. Through the more detailed description of some embodiments of the present disclosure in the accompanying drawings, the above and other features and advantages of the present disclosure will become more apparent.

DETAILED DESCRIPTION

Techniques are provided for extracting and annotating entity and non-entity information in order to improve predictive analytics in a cognitive system.

Figure 1:
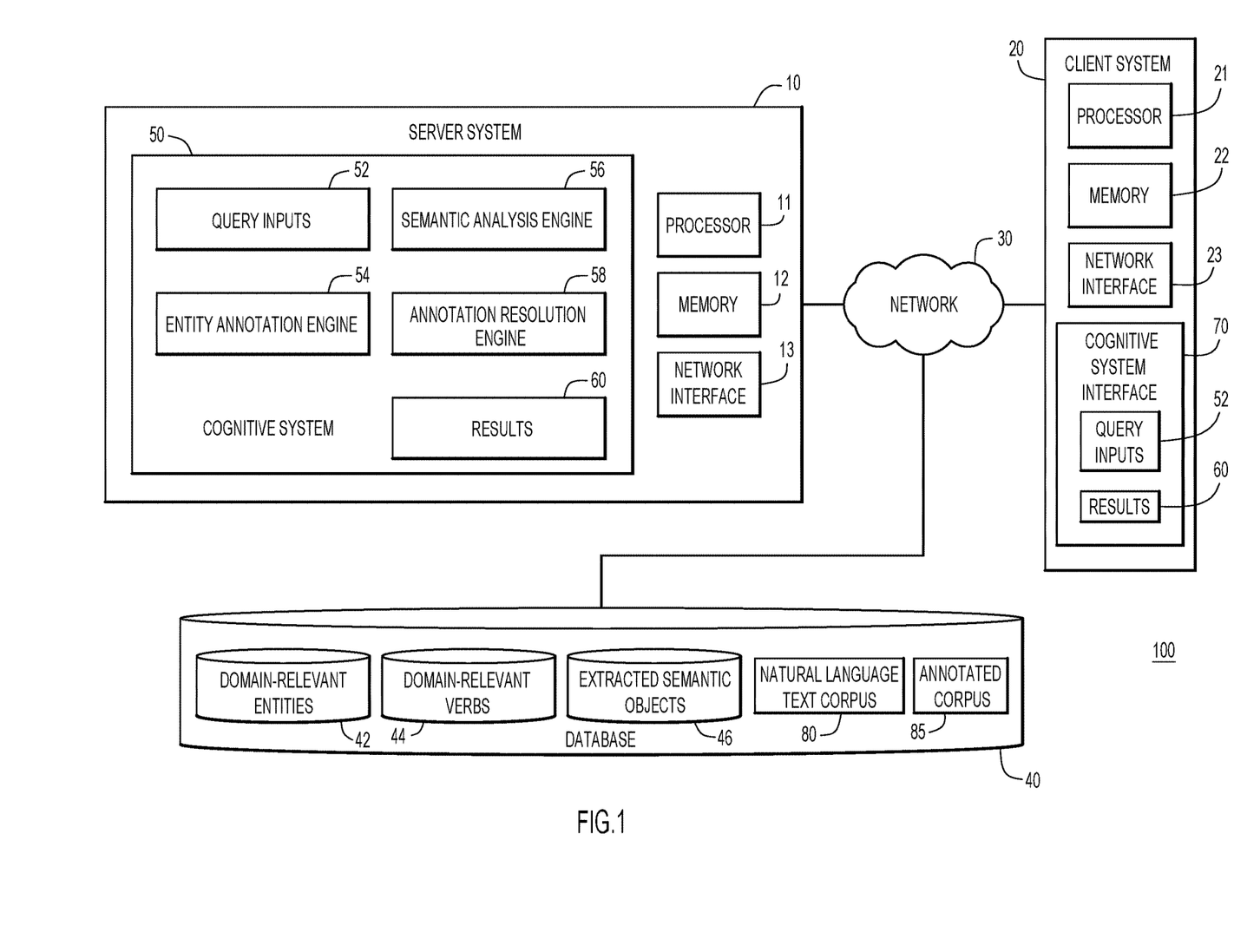
FIG. 1 is a block diagram of an example computing environment for using entity and non-entity relationships for predictive analytics in accordance with embodiments of the present disclosure.

An example environment 100 for use with present invention embodiments is illustrated in FIG. 1. Specifically, the environment includes one or more server system(s) 10, and one or more client or end-user system(s) 20. Server system 10 and client system 20 may be remote from each other and may communicate over a network 30. The network may be implemented by any number of any suitable communications media (e.g., wide area network (WAN), local area network (LAN), Internet, Intranet, etc.). Alternatively, server system 10 and client system 20 may be local to each other, and may communicate via any appropriate local communication medium (e.g., local area network (LAN), hardwire, wireless link, Intranet, etc.).

Client system 20 enables users to submit queries (e.g., queries for predictive analytics, etc.) to server system 10 to generate predictions based upon an analysis of a large corpus of data (e.g., scientific data, scientific journals, publically and/or privately accessible chemical databases, databases of known pharmaceutical and/or biologic therapeutic compounds, databases/literature of known genes/DNA, databases/literature of expressed RNA, databases/literature covering proteomics, databases/literature covering metabolomics, etc.). In some aspects, users can input query terms (e.g., cancer genes, drugs to treat diseases, chemical compounds, proteins, biologics, diseases, etc.), and the system 100 will return entities and non-entities predicted to be related to the query The server system 10 includes a cognitive system 50 to generate predictions based upon analysis of a large corpus of data in response to a query. A query may be received as query inputs 52. A database system 40 may store various types of information for the analysis (e.g., domain-relevant entities 42, domain-relevant verbs 44, extracted semantic objects 46, natural language text corpus 80, annotated corpus 85, etc.). Database 40 may also store any data generated by server system 10, including entity information extracted by the entity annotation engine 54, semantic object and semantic relationship information extracted by semantic analysis engine 56, and non-entity to entity resolution information by annotation resolution engine 58. The database system 40 may be implemented by any conventional or other database or storage unit, may be local to or remote from server system 10 and client system 20, and may communicate via any appropriate communication medium (e.g., local area network (LAN), wide area network (WAN), Internet, hardwire, wireless link, Intranet, etc.).

Server system 10 and client system 20 may be implemented by any conventional or other computer systems preferably equipped with a display or monitor, a base (e.g., including at least one hardware processor 11, 21 (e.g., microprocessor, controller, central processing unit (CPU), etc.), one or more memories 12, 22 and/or internal or external network interfaces or communications devices 13, 23, (e.g., modem, network cards, etc.) respectfully), along with optional input devices (e.g., a keyboard, mouse or other input device), and any commercially available and custom software (e.g., cognitive system 50, server/communications software, browser/interface software, etc.). Server system 10 comprises cognitive system 50, which includes query inputs 52, entity annotation engine 54, semantic analysis engine 56, and annotation resolution engine 58 as described herein. In some embodiments, results 60 are provided to the client system 20 for display to a user, wherein the results may comprise entities and non-entities, e.g., in a knowledge graph or other format, in response to a user query.

In other embodiments, a graphical representation of the results may be provided to the user (e.g., a network of nodes, knowledge graph, etc.). Client system 20 may present a graphical user (e.g., GUI, etc.) or other cognitive system interface 70 (e.g., command line prompts, menu screens, etc.) to solicit information from users pertaining to the desired analysis, and may provide reports (e.g., lists, spreadsheets, graphical results, etc.) including analysis results 60 (e.g., predicted relationships between entities and non-entities, predicted relationships between non-entities and non-entities, predicted relationships between entities and other entities etc.).

Alternatively, one or more client systems 20 may analyze a corpus of documents to generate predictive analytics (e.g., predicted relationships between entities and non-entities, predicted relationships between non-entities and non-entities, predicted relationships between entities and other entities, etc.) when operating as a stand-alone unit. In a stand-alone mode of operation, the client system stores or has access to the data (e.g., database 40, including natural language text corpus 80 stored on database 40), and includes a cognitive system 50 to generate predictive analytics. The graphical user (e.g., GUI, etc.) or other interface 70 (e.g., command line prompts, menu screens, etc.) solicits information from a corresponding user pertaining to the desired documents and analysis for input into the cognitive system 50, and may provide reports and/or analysis results 60 to the user.

Cognitive system 60 may include one or more modules or units to perform the various functions of present invention embodiments described herein. The various modules (e.g., query inputs 52, entity annotation engine 54, semantic analysis engine 56, annotation resolution engine 58, etc.) may be implemented by any combination of any quantity of software and/or hardware modules or units, and may reside within memory 12 of the server for execution by processor 11.

In some aspects, query inputs 52 may include query terms provided by the user. The query terms may include entity input and non-entity inputs. Present invention embodiments allow a user to perform a search with the entity term, and/or with the non-entity term as the initial search criteria, and to expand any search by subsequent inclusion of entity and non-entity terms in an equivalent manner.

Entity annotation engine 54 may utilize natural language processing to extract known entities from a corpus of data 80. In some cases, the natural language processing component of the entity annotation engine may utilize machine learning to identify entities for extraction.

Annotation may occur in an automated or semi-automated manner. For instance, a machine learning system may be provided with a training data set, with which to learn and apply rules for extracting and classifying entities. A curator may review the annotations/classifications to verify that proper annotation/classification has occurred, and additional training data may be provided in cases in which misclassifications are discovered.

It should be noted that the system and method presented herein may furthermore be extended to include any type of entity-specific data representations, such as sequence data for proteins and other macromolecules, or may be extended to include entity-specific information for non-life sciences entities.

Semantic analysis engine 56 may extract domain-relevant verbs 44 and semantic objects 46 (e.g., subject, object, or other nouns, etc.), to capture non-entities and their associated context by analysis of the corpus of text based data. For a non-entity identified in a document, the context of the entity within the document can be semantically analyzed, e.g., by decomposing words and/or phrases (e.g., into nouns, verbs, objects, adjectives, adverbs, etc.) into terms used in the local or global vicinity of the semantic object to establish the context of the non-entity.

In some embodiments, the semantic analysis engine 56 may comprise a machine learning component to identify and extract semantic objects to provide to the annotation resolution engine 58. Annotation resolution engine 58 may consolidate duplicate and/or overlapping entities (see also, FIG. 4).

Figure 2:
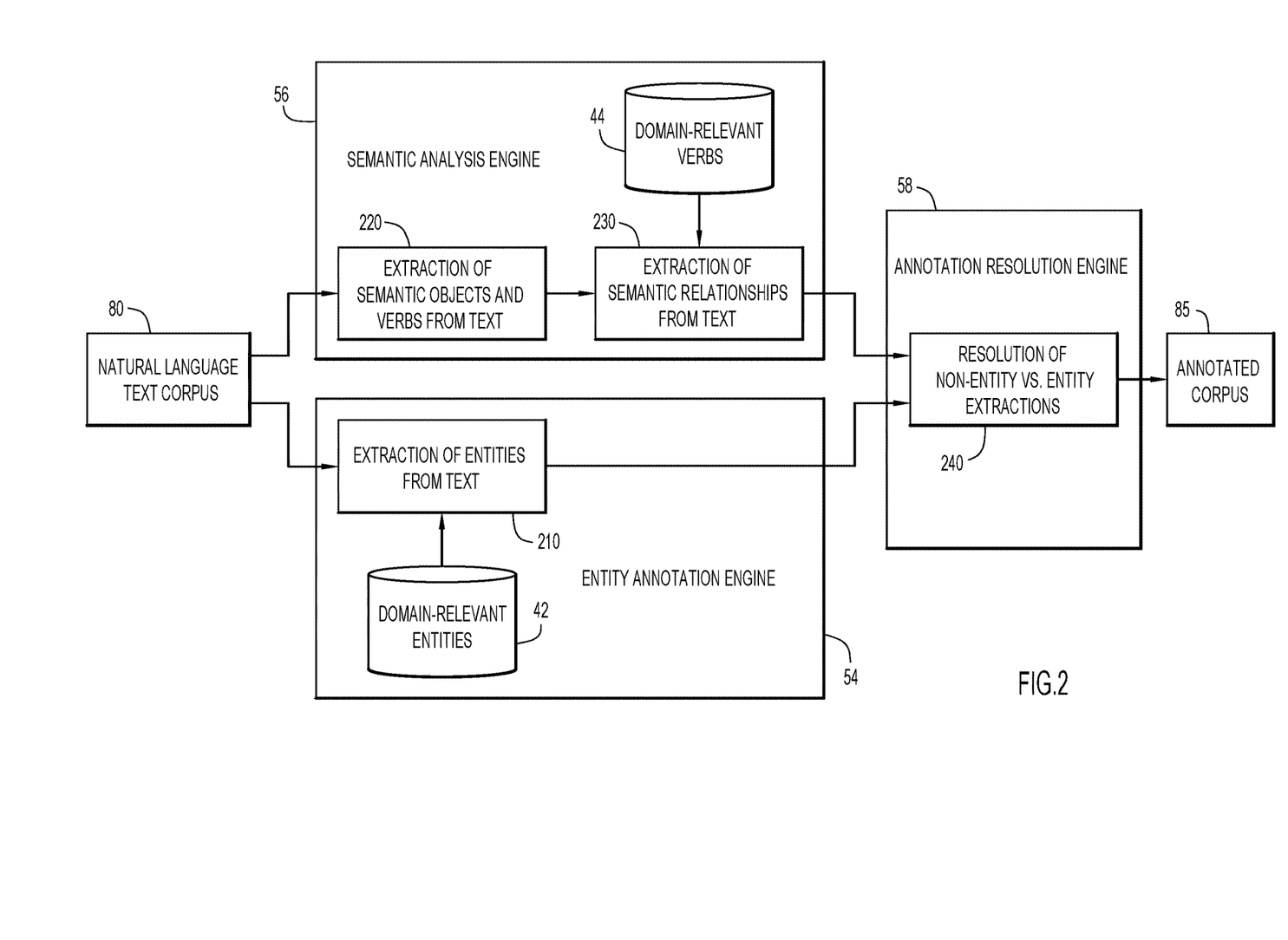
FIG. 2 is an illustration showing extraction and annotation of entity and non-entity information, in accordance with embodiments of the present disclosure.

FIG. 2 is an example illustration showing generation of an annotated corpus 85 of information comprising entity and non-entity information, in accordance with embodiments of the present disclosure.

Semantic relationship connections may be formed between non-entities and other non-entities, as well as between non-entities and entities. When utilized in combination with semantic relationship connections between entities, this feature allows an enhanced understanding of the semantic context of and interactions between entities and non-entities as well as between non-entities and other non-entities. The addition of non-entity-based connections can be considered an increase in the dimensionality of the semantic relationship network, from one- to two-dimensional analysis.

As shown in FIG. 2, a natural language text corpus 80 may be processed by an entity annotation engine 54 and a semantic analysis engine 56. At operation 210, entity annotation engine 54 extracts entities from the natural language text corpus 80, e.g., based on domain relevant entities 42 which may be stored in database 40. Domain relevant entities 42 represent entities having a known relationship to other entities and may be used as inputs for analyzing the natural language text corpus. In some aspects, domain relevant entities database 42 may comprise the names of extracted entities (e.g., a gene, a protein, a drug, a disease, or any other suitable category, etc.) that may have previously been extracted and curated, and the entity annotation engine 54 may use these domain relevant entities 42 as inputs to search for information pertaining to these specific entities within the corpus of documents. The extracted entities are provided to an annotation resolution engine 58.

At operation 220, the semantic analysis engine 56 extracts semantic objects (e.g., subjects, objects, or other nouns) and verbs from the corresponding natural language text corpus 80. In some aspects, machine learning methods and systems may be used to extract semantic objects from the text, (e.g., by identifying subject-verb-object structures).

At operation 230, the semantic analysis engine 56 extracts semantic relationships from text corpus 80, e.g., to understand the context of the extracted semantic objects. For example, semantic relationships may be identified by parsing sentences and identifying language motifs or language structures, such as subject(S), verb(V), object(O) structures. Although the examples provided herein reference language structures that are subject-verb-object (SVO), this is merely an example, and many other types of language structures from linguistics terminology are contemplated for use herein.

In some aspects, the semantic analysis engine 56 may determine the context of extracted semantic objects (e.g., based on subject-verb-object structure). For example, a context can be determined locally (by extracting words local to the object of interest) or globally (by evaluating the context of a semantic object globally within a document) as provided herein.

Natural language processing or machine learning methods may also be used to extract and understand semantic relationships. Domain-relevant verbs database 44 contains known verbs used to characterize and understand semantic relationships, e.g., the verbs inhibit, activate, cause, contribute, etc. may be compared to the extracted semantic objects and verbs from operation 220, to determine context. Additional phrases in the proximity of the extracted semantic objects and verbs may be considered as well. For instance, for the phrase "aspirin treats different conditions", a semantic relationship may be identified between the subject "aspirin" and object "different conditions" by a pattern-matching rule that detects "treats" as a verb (domain relevant verb) linking the subject ("aspirin") to the object ("different conditions"). In some aspects, the type of semantic relationship may be established by the verb form, so for example, the verb "inhibits" may indicate a negative influence while the verb "activates" may indicate a positive influence. The semantic relationships are then provided to the annotation resolution engine 58.

At operation 240, the annotation resolution engine 58 resolves entity and non-entity information based on the extracted semantic objects and verbs from operation 220, semantic relationships from operation 230, and extracted entities from operation 210 to produce an annotated corpus 85. Resolution of non-entity versus entity annotations also prevents misleading or redundant semantic connections. This process is further described in FIG. 4.

In some aspects, the entity annotation engine 54 and semantic analysis engine 56 may store extracted information (e.g., extracted entities, language motifs or structures to identify semantic objects, phrases surrounding the semantic object, etc.) in database 40. In some embodiments, the entity annotation engine 54 and semantic analysis engine 56 may extract data from available databases and systems, from documents provided by the user, or both. The extracted information for user provided documents may also be provided to annotation resolution engine 58 for annotation.

Figure 3:
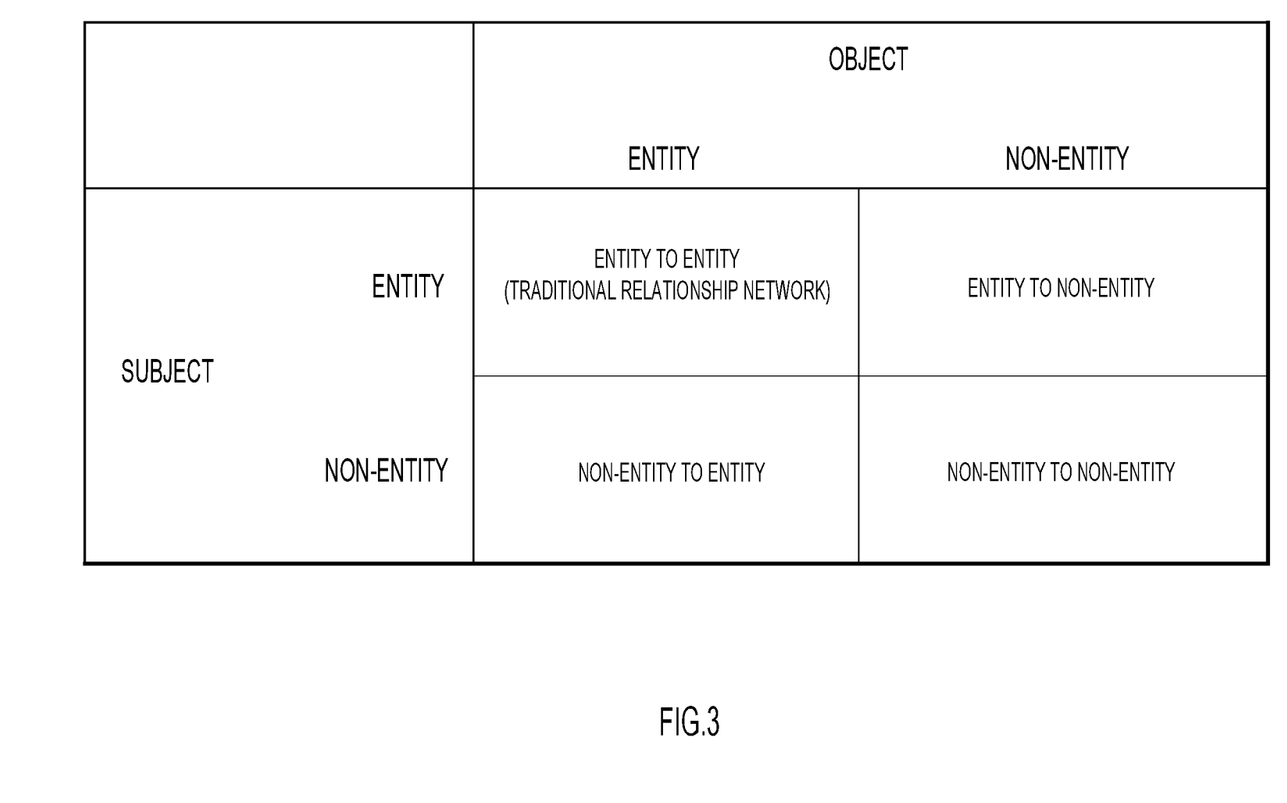
FIG. 3 is a chart showing entity and non-entity relationships, according to embodiments of the present disclosure.

FIG. 3 shows a chart of different relationships between subjects and objects according to aspects of the present invention. A traditional semantic network of connections maps only entities to entities. However, this captures a fraction of available information. For example, the language structure "subject-verb-object" may additionally comprise a subject that is an entity and an object that is a non-entity, a subject that is a non-entity and an object that is an entity, or a subject that is a non-entity and an object that is a non-entity. Each of these three types of information are not captured using only entity to entity relationships. Present invention embodiments provide techniques for capturing this additional information, and for providing a more complete understanding of the semantic context of entities and non-entities when performing searches in a network of semantic connections.

Figure 4:
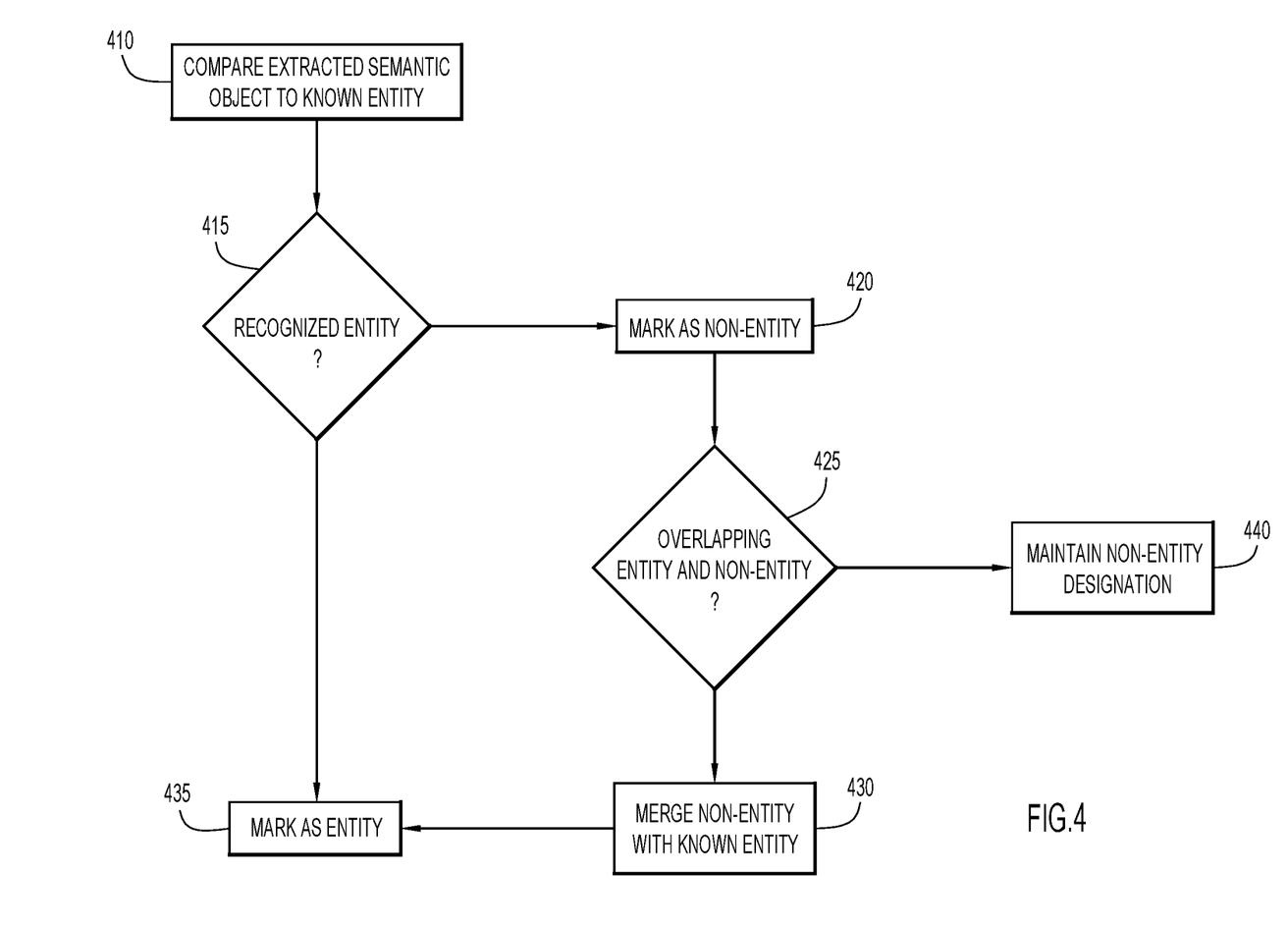
FIG. 4 is a flowchart of operations for resolving entities and non-entities, according to embodiments of the present disclosure.

Referring to FIG. 4, a flowchart of example operations involving entity annotation by annotation resolution engine 58 are shown according to aspects of the invention. At operation 410, semantic objects (e.g., subjects, objects, or other nouns) are compared to known domain-relevant entities 42. At operation 415, a determination is made as to whether the semantic object is a recognized entity, e.g., matches an entity in domain-relevant entities 42. If the semantic object is a recognized entity, then the semantic objects is marked as an entity at operation 435. Otherwise, if the semantic object is not an entity, the semantic object is marked as a non-entity at operation 420. While unrecognized semantic objects are initially considered as non-entities for the purpose of semantic relationship extraction, this determination may be revised by cross-referencing the entity and non-entity annotations. At operation 425, the non-entity is evaluated to determine if it overlaps with a known entity. Entity annotations, being domain-specific, are generally considered to be of greater relevance and consequently are given preference in the event of overlapping non-entity and entity annotations. For example, a non-entity annotation of "light" may be removed from consideration if it is found to overlap with an entity annotation, such as a medical condition, "light sensitivity". In the event of overlapping annotations, at operation 430, the semantic relationships of the non-entity may be merged with the corresponding entity, so as to avoid information loss. For example, the preserved entity annotation may inherit the semantic relationships assigned to the overlapping non-entity to be removed, which can serve to prevent loss of semantic connections in general as well as increase the specificity or domain relevance of a particular semantic connection. At operation 435, the overlapping non-entity is removed, and the recognized entity remaining. If the non-entity is not overlapping, the non-entity designation is maintained at operation 440.

The annotated corpus 85 may be analyzed to provide connections between the entities and non-entities and to facilitate discovery of novel relationships. In some aspects, the non-entities may be displayed as entity type nodes in a knowledge graph.

In some aspects, the knowledge graph comprises a plurality of entity nodes with at least one entity node associated with an undefined entity. The knowledge graph may be traversed to identify one or more relationships from a group of relationships between defined entities, relationships between undefined entities, and relationships between defined and undefined entities.

Figure 5:
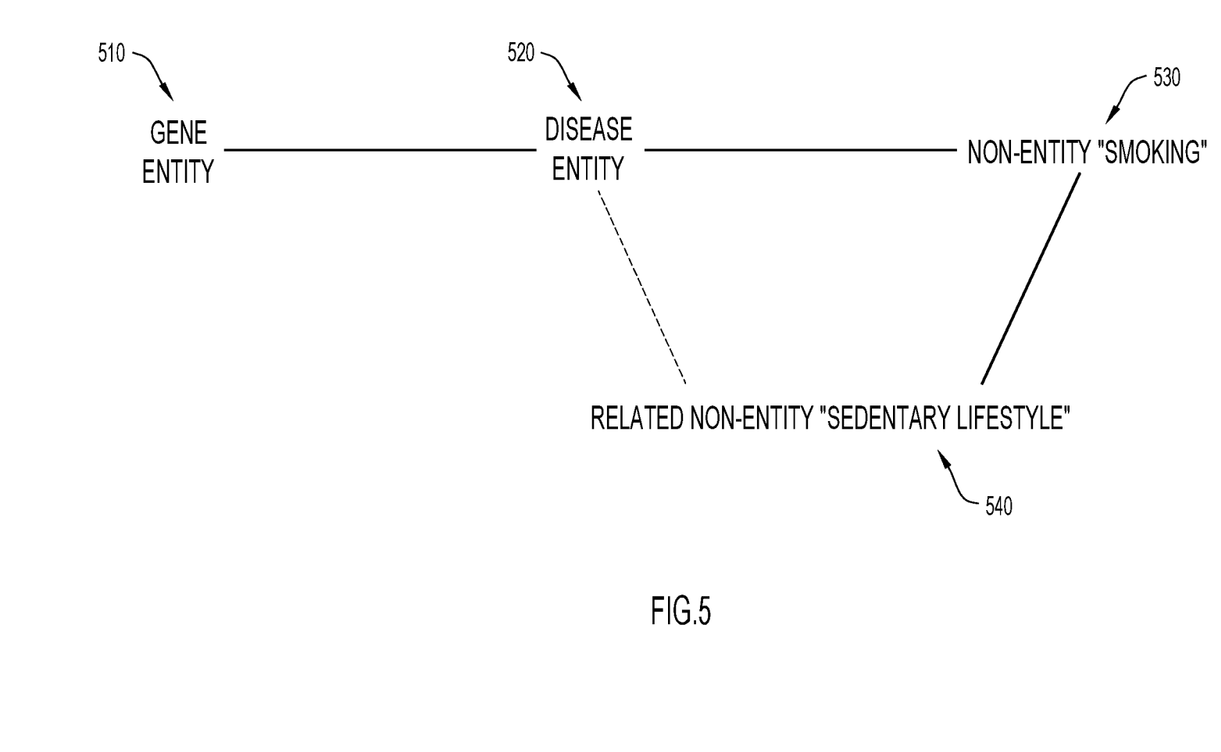
FIG. 5 is an example of utilizing entity and non-entity information to generate complex predictive analytics, according to embodiments of the present disclosure.

FIG. 5 shows an example of identifying novel relationships using the techniques provided herein. For example, a semantic relationship network may comprise connections between gene entity 510 and disease entity 520 mined from unstructured text. Additionally, there may be non-entity information, e.g., identified by extracted phrases that are neither genes nor diseases, but which are discussed in a specific semantic context of a gene or a disease. For instance, the language structure "smoking increases the risk of <a disease>" may establish a semantic relationship in which non-entity 530 "smoking" increases the risk of another disease. Another language structure may be extracted which links non-entity 530 to a related non-entity 540. For example, the language structure "smoking is correlated with a sedentary lifestyle", connects the non-entity "smoking" to another related non-entity "a sedentary lifestyle". In this example, "<a disease>" is connected to a related non-entity via two nodes: a disease is connected to "smoking" and smoking is connected to "sedentary". This relationships allows insights to be derived about the association of "<a disease>" with "sedentary", and so on. Thus, a novel relationship between a disease and another related non-entity may be discovered using the present techniques. Although this example identifies connections in two steps, novel relationships may also be identified using three steps, four steps, five steps or more.

This kind of contextual understanding could not be extracted from a traditional semantic relationship network limited to connections between entities. Furthermore, providing this information within the framework of a semantic relationship network enables these connections to be visualized by a node-link diagram or tabular visualization, alongside the traditional entity connections, facilitating understanding of the relationships between entities and non-entities.

In some aspects, within a large corpus of information, multiple semantic relationships between a particular object and a particular subject may be present. For example, an object may be represented as activating in one source and inhibiting in another source with reference to the same subject. Thus, in some cases, the extracted semantic information may be conflicting. In some aspects, the conflicting semantic information may be aggregated into representative categories and displayed separately, e.g., references in which the object is activating towards the subject may be displayed separately from references in which the object is inhibiting towards the subject. In other aspects, conflicting information may be combined and associated with a value, wherein the magnitude of the value indicates whether the relationship is inhibitory, activating or mixed. In this example, the resulting data set may be represented as a knowledge graph of entity nodes with a first entity node associated with an undefined entity and a first relationship with the entity (e.g., an inhibitory relationship between an entity and a non-entity), and a second entity node associated with an undefined entity and a second relationship with the same entity (e.g., an activating relationship between an entity and a non-entity).

In other aspects, non-entities identified by the system may be flagged as candidates for conversion to entities. For example, if a non-entity shows up at a high frequency in a population of documents, the non-entity may be a candidate for conversion into an entity. The non-entity may be flagged by the system as a candidate for conversion, and may be subsequently converted into an entity, e.g., upon user review and curation. In other aspects, the system may group non-entities together, into new categories, which may also serve as candidate entities, and may facilitate discovery of new relationships between entities and non-entities.

In yet another example application of the system, in cases in which a large number of potential drug candidates are available as leads for a pharmaceutical compound, the system may identify compounds that are more likely to be successful or less likely to be successful based upon semantic information across a corpus of documents. For example, the system may analyze information in the corpus, including but not limited to, toxicity of specific elements or structures in the compound, structures which are similar to other compounds that have been successful or unsuccessful in other studies, etc. This information may be combined, e.g., using a weighting scheme, in order to rank individual candidate compounds. Alternatively, the information may be presented in a display for presentation to a user. Semantic analysis across a corpus of data allows generation of leads that would otherwise not be apparent, and the techniques presented herein allow consideration of both entity and non-entity information allowing improved predictions. Accordingly, for a large number of potential leads (entities or non-entities), e.g., for a pharmaceutical drug lead, the system facilitates identification of optimal leads based upon entity and non-entity data.

Figure 6:
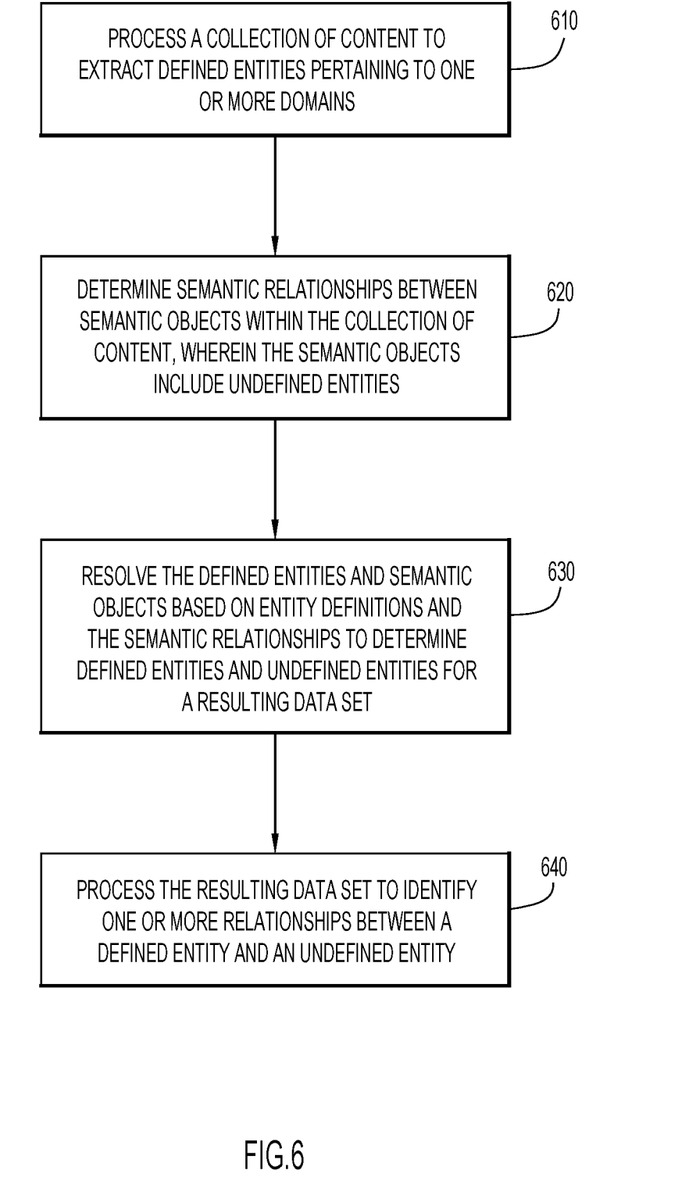
FIG. 6 is a flowchart of operations for extracting and annotating entity and non-entity information, according to embodiments of the present disclosure.

FIG. 6 shows a flowchart of operations for making predictions using entities and non-entities, according to embodiments of the present disclosure. At operation 610, a collection of content is processed to extract defined entities pertaining to one or more domains. At operation 620, semantic relationships between semantic objects are determined within the collection of content, wherein the semantic objects include undefined entities. At operation 630, the defined entities and semantic objects are resolved based on entity definitions and the semantic relationships to determine defined entities and undefined entities for a resulting data set. At operation 640, the resulting data set is processed to identify one or more relationships between a defined entity and an undefined entity.

Present embodiments offer significant improvements over traditional approaches. Capturing this additional contextual information using an established entity network approach, wherein only entities are considered, would require creating a new annotator or modifying an existing annotator to recognize each new term or group of terms of interest, and then running that annotator against all content to create the new entity annotations. This traditional approach is highly inefficient as it requires both additional development based on pre-specified knowledge to be discovered, and additional annotation processing. Present invention embodiments bypass this inefficiency, allowing instead for efficient search and analytics using non-entity phrases at runtime.

Accordingly, present invention embodiments may be used as part of a predictive analytics system and/or methodology to generate predictions based upon the analysis of a corpus of information including both entities and non-entities. Present invention embodiments also allow for both entities and non-entities to be searched across a corpus of data. Accordingly, entity to entity relationships, entity to non-entity relationships, and non-entity to non-entity relationships may each be considered when making inferences and predictions on information from processing millions or tens of millions of documents. These techniques allow novel relationships to be discovered from searching complex feature spaces that are not otherwise evident. Additionally, such novel relationships may be discovered, in real time or near real time, as inputs may be changed and adjusted in real time to tailor search results to particular queries.

The embodiments provided herein allow for complex predictions to be generated by utilizing multi-dimensional data. These techniques may be utilized to provide a more complete and robust predictive analytics capability using both entity and non-entity information. Predictions may be tested experimentally, and the results of the predictions provided to the cognitive system 50, in order to continually improve and refine predictive abilities.

The embodiments provided herein may be applied to the field of chemical informatics, wherein the entities may be small molecules, as well as the field of biologics, wherein the entities may be genes, proteins, antibodies, peptides, or any other biologic macromolecule for which structural information or semantic information may be available. Predictive analytics may be used to identify molecules involved in the formation and/or progression of a disease or disorder as well as entities that may be useful in treating said diseases or disorders. Non-entity information may be used to identify factors and related factors affecting the progression of a disease.

It will be appreciated that the embodiments described above and illustrated in the drawings represent only a few of the many ways of implementing embodiments for combining entities with non-entities to improve predictive analytics. It will also be appreciated that the methods provided herein are implemented by a computer as part of a cognitive system.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, cognitive system 50, cognitive system interface 70, etc.). These systems may include any types of monitors and input devices (e.g., keyboard, mouse, voice recognition, etc.) to enter and/or view information.

It is to be understood that the software (e.g., cognitive system 50, cognitive system interface 70, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., cognitive system 50, cognitive system interface 70, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., domain relevant entities 42, domain relevant verbs 44, extracted semantic objects 46, natural language text corpus 80, annotated corpus 85, and any other information including query inputs, results of predictive analytics, etc.). The database system may be implemented by any number of any conventional or other databases, data stores or storage structures (e.g., files, databases, data structures, data or other repositories, etc.) to store information (e.g., domain relevant entities 42, domain relevant verbs 44, extracted semantic objects 46, natural language text corpus 80, annotated corpus 85, and any other information including query inputs, results of predictive analytics, etc.). The database system may be included within or coupled to the server and/or client systems. The database systems and/or storage structures may be remote from or local to the computer or other processing systems, and may store any desired data (e.g., domain relevant entities 42, domain relevant verbs 44, extracted semantic objects 46, natural language text corpus 80, annotated corpus 85, and any other information including query inputs, results of predictive analytics, etc.).

The present invention embodiments may employ any number of any type of user interface (e.g., Graphical User Interface (GUI), command-line, prompt, etc.) for obtaining or providing information (e.g., domain relevant entities 42, domain relevant verbs 44, extracted semantic objects 46, natural language text corpus 80, annotated corpus 85, and any other information including query inputs, results of predictive analytics, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The results may include any information arranged in any fashion, and may be configurable based on rules or other criteria to provide desired information to a user (e.g., domain relevant entities 42, domain relevant verbs 44, extracted semantic objects 46, natural language text corpus 80, annotated corpus 85, and any other information including query inputs, results of predictive analytics, etc.).

The present invention embodiments are not limited to the specific tasks or algorithms described above, but may be utilized for any system in which multidimensional analysis is desired, e.g., for documents comprising entities and non-entities.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method, in a cognitive data processing system comprising at least one processor and at least one memory, the at least one memory comprising instructions executed by the at least one processor to cause the at least one processor to implement a predictive analytics system, the method comprising:
    obtaining a list of defined entities pertaining to one or more domains, wherein a defined entity comprises an entity that has a known relationship to another entity on the list;
    processing a collection of content to identify information based on a semantic context of the defined entities, and performing semantic analysis on the identified information to extract sematic objects comprising the defined entities;
    determining semantic relationships between the semantic objects within the collection of content, wherein the semantic objects include undefined entities related to a defined entity based on the semantic context and the semantic relationships include conflicting relationships for corresponding semantic objects, and wherein the conflicting relationships include an activating relationship between the defined entity and a corresponding undefined entity and an inhibiting relationship between the defined entity and the corresponding undefined entity;
    combining the conflicting relationships to produce a value, wherein a magnitude of the value indicates a resulting semantic relationship for the corresponding semantic objects, and wherein the resulting semantic relationship includes one of the activating relationship and the inhibiting relationship;
    converting one or more of the undefined entities to the defined entities based on a frequency of occurrence of the one or more undefined entities within the collection of content exceeding a number of occurrences;
    resolving the defined entities and the semantic objects based on entity definitions and the semantic relationships to determine defined entities and undefined entities for a resulting data set;
    identifying, in the resulting data set, an undefined entity with an entity name that contains one or more terms of an entity name of a corresponding defined entity, merging the undefined entity with the corresponding defined entity, wherein the semantic relationships of the undefined entity to other undefined and defined entities are inherited by the corresponding defined entity, and removing the undefined entity from the resulting data set after merging;
    processing the resulting data set to form connections between the defined entities and the undefined entities based on the semantic relationships; and
    identifying one or more relationships between the defined entities and the undefined entities or between the undefined entities based on the connections.

2. The method of claim 1, wherein resolving the defined entities and the semantic objects further comprises:
    annotating the defined and undefined entities in the resulting data set.

3. The method of claim 2, wherein resolving the defined entities and the semantic objects further comprises:
    verifying a semantic object against entity definitions to annotate the semantic object as one of a defined entity and an undefined entity.

4. The method of claim 1, wherein determining semantic relationships further comprises:
    parsing sentences within the collection of content and recognizing parts of speech structures.

5. The method of claim 1, wherein the resulting data set is represented as a knowledge graph of entity nodes with at least one entity node associated with an undefined entity, and processing the resulting data set further comprises:
  traversing the knowledge graph to identify relationships between undefined entities, and relationships between defined and undefined entities.

6. The method of claim 1, wherein a defined entity includes a gene, a disease, a drug, or a biologic compound and an undefined entity includes an associated medical condition.

7. The method of claim 1, wherein the resulting data set is represented as a knowledge graph of entity nodes and further comprising:
  identifying conflicting semantic information for an entity node and categorizing the conflicting information into two or more categories;
  for each category, associating a node with the entity node to represent each category of conflicting information.

8. A system for predictive analytics comprising at least one processor configured to:
  obtain a list of defined entities pertaining to one or more domains, wherein a defined entity comprises an entity that has a known relationship to another entity on the list;
  process a collection of content to identify information based on a semantic context of the defined entities, and perform semantic analysis on the identified information to extract semantic objects comprising the defined entities;
  determine semantic relationships between the semantic objects within the collection of content, wherein the semantic objects include undefined entities related to a defined entity based on the semantic context and the semantic relationships include conflicting relationships for corresponding semantic objects, and wherein the conflicting relationships include an activating relationship between the defined entity and a corresponding undefined entity and an inhibiting relationship between the defined entity and the corresponding undefined entity;
  combine the conflicting relationships to produce a value, wherein a magnitude of the value indicates a resulting semantic relationship for the corresponding semantic objects, and wherein the resulting semantic relationship includes one of the activating relationship and the inhibiting relationship;
  convert one or more of the undefined entities to the defined entities based on a frequency of occurrence of the one or more undefined entities within the collection of content exceeding a number of occurrences;
  resolve the defined entities and the semantic objects based on entity definitions and the semantic relationships to determine defined entities and undefined entities for a resulting data set;
  identify, in the resulting data set, an undefined entity with an entity name that contains one or more terms of an entity name of a corresponding defined entity, merge the undefined entity with the corresponding defined entity, wherein the semantic relationships of the undefined entity to other undefined and defined entities are inherited by the corresponding defined entity, and remove the undefined entity from the resulting data set after merging;
  process the resulting data set to form connections between the defined entities and the undefined entities based on the semantic analysis; and
  identify one or more relationships between the defined entities and the undefined entities or between the undefined entities based on the connections.

9. The system of claim 8, wherein the at least one processor is further configured to resolve the defined entities and the semantic objects by annotating the defined and undefined entities in the resulting data set.

10. The system of claim 9, wherein the at least one processor is further configured to resolve the defined entities and the semantic objects by verifying an object against entity definitions to annotate the object as one of a defined entity and an undefined entity.

11. The system of claim 8, wherein the at least one processor is further configured to:
  identify subject-verb-object language structures in the collection of content to extract the semantic objects, wherein the semantic objects each include one of a subject, verb, object, and other noun; and
  determine semantic relationships between the defined and undefined entities based on the identified subject-verb-object language structures, wherein the verb of an identified subject-verb-object structure indicates a known semantic relationship, and wherein the subject and the object of the identified subject-verb-object structure indicate the defined and undefined entities related by the known semantic relationship.

12. The system of claim 8, wherein the resulting data set is represented as a knowledge graph of entity nodes with at least one entity node associated with an undefined entity, and the at least one processor is further configured to resolve the defined entities and the semantic objects by processing the resulting data set by traversing the knowledge graph to identify relationships between undefined entities, and relationships between defined and undefined entities.

13. The system of claim 8, wherein a defined entity includes a gene, a disease, a drug, or a biologic compound and an undefined entity includes an associated medical condition.

14. The system of claim 8, wherein the resulting data set is represented as a knowledge graph of entity nodes and the at least one processor is further configured for:
  identifying conflicting semantic information for an entity node and categorizing the conflicting information into two or more categories;
  for each category, associating a node with the entity node to represent each category of conflicting information.

15. A computer program product for predictive analytics, the computer program product comprising one or more computer readable storage media collectively having program instructions embodied therewith, the program instructions executable by a processor to:
  obtain a list of defined entities pertaining to one or more domains, wherein a defined entity comprises an entity that has a known relationship to another entity on the list;
  process a collection of content to identify information based on a semantic context of the defined entities, and perform semantic analysis on the identified information to extract semantic objects comprising the defined entities;
  determine semantic relationships between the semantic objects within the collection of content, wherein the semantic objects include undefined entities related to a defined entity based on the semantic context and the semantic relationships include conflicting relationships for corresponding semantic objects, and wherein the conflicting relationships include an activating relationship between the defined entity and a corresponding undefined entity and an inhibiting relationship between the defined entity and the corresponding undefined entity;

combine the conflicting relationships to produce a value, wherein a magnitude of the value indicates a resulting semantic relationship for the corresponding semantic objects, and wherein the resulting semantic relationship includes one of the activating relationship and the inhibiting relationship;

convert one or more of the undefined entities to the defined entities based on a frequency of occurrence of the one or more undefined entities within the collection of content exceeding a number of occurrences;

resolve the defined entities and the semantic objects based on entity definitions and the semantic relationships to determine defined entities and undefined entities for a resulting data set;

identify, in the resulting data set, an undefined entity with an entity name that contains one or more terms of an entity name of a corresponding defined entity, merge the undefined entity with the corresponding defined entity, wherein the semantic relationships of the undefined entity to other undefined and defined entities are inherited by the corresponding defined entity, and remove the undefined entity from the resulting data set after merging;

process the resulting data set to form connections between the defined entities and the undefined entities based on the semantic analysis; and identify one or more relationships between the defined entities and the undefined entities or between the undefined entities based on the connections.

16. The computer program product of claim 15, wherein the program instructions are executable to resolve the defined entities and the semantic objects by annotating the defined and undefined entities in the resulting data set.

17. The computer program product of claim 15, wherein the program instructions are executable to resolve the defined entities and the semantic objects by verifying an object against entity definitions to annotate the object as one of a defined entity and an undefined entity.

18. The computer program product of claim 15, wherein the program instructions are executable to determine semantic relationships by parsing sentences within the collection of content and recognizing parts of speech structures.

19. The computer program product of claim 15, wherein the resulting data set is represented as a knowledge graph of entity nodes with at least one entity node associated with an undefined entity, and wherein the program instructions are executable to resolve the defined entities and the semantic objects by processing the resulting data set by traversing the knowledge graph to identify relationships between undefined entities, and relationships between defined and undefined entities.

20. The computer program product of claim 15, wherein a defined entity includes a gene, a disease, a drug, or a biologic compound and an undefined entity includes an associated medical condition.

* * * * *